(12) United States Patent
Brothers et al.

(10) Patent No.: US 6,395,937 B2
(45) Date of Patent: May 28, 2002

(54) SYNTHESIS OF DIACYL PEROXIDE IN CARBON DIOXIDE

(75) Inventors: Paul Douglas Brothers, Chadds Ford, PA (US); Brian Edward Kipp; Charles Joseph Noelke, both of Wilmington, DE (US); Ronald Earl Uschold, West Chester, PA (US); Robert Clayton Wheland, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/850,547

(22) Filed: May 7, 2001

Related U.S. Application Data

(60) Provisional application No. 60/207,004, filed on May 25, 2000.

(51) Int. Cl.[7] .............................................. C07C 407/00
(52) U.S. Cl. ...................... 568/566; 568/568; 568/560
(58) Field of Search ................................ 568/558, 560, 568/566

(56) References Cited

U.S. PATENT DOCUMENTS

| | | | |
|---|---|---|---|
| 2,771,492 A | * | 11/1956 | Chapman et al. |
| 3,100,803 A | * | 8/1963 | Porter et al. |
| 5,021,516 A | | 6/1991 | Wheland |
| 5,820,841 A | | 10/1998 | Chen et al. |

FOREIGN PATENT DOCUMENTS

| | | |
|---|---|---|
| JP | 61-152653 | 7/1986 |

OTHER PUBLICATIONS

CA:77:139514 abs of Tr Khim Khim Teknol by Moryganov et al 1971 (L) pp 152–5, 1971.*

S.R. Sandler and W. Karo, (1974) Polymer Synthesis vol. 1, Academic Press, Inc., Orlando, Florida, p. 451.

A. McKillop and W. R. Sanderson, Tetrahedron, vol. 51, No. 22, pp. 6145–6166, 1995.

J. Muzart, Synthesis, pp. 1325–1346, Nov. 1995.

M. S. Cooper, et al. Synlett, pp. 533–535, Sep. 1990.

J.T. Kadia et al., Polymer Preparation, vol. 39, No. 2, pp. 835–836, 1998.

* cited by examiner

Primary Examiner—Jean F. Vollano

(57) ABSTRACT

This invention relates to a process for the synthesis of diacyl peroxide by contacting acyl halide and peroxide complex in liquid or supercritical carbon dioxide.

16 Claims, No Drawings

SYNTHESIS OF DIACYL PEROXIDE IN CARBON DIOXIDE

This application claims priority to provisional application No. 60/207,004, filed May 25, 2000.

FIELD OF THE INVENTION

This invention is in the field of the synthesis of diacyl peroxide from acyl halide in liquid or supercritical carbon dioxide.

BACKGROUND OF THE INVENTION

Diacyl peroxides are among the commonly used initiators in the commercial production of polyolefins, particularly fluoroolefins, such as tetrafluoroethylene. They may be represented as R—(C=O)—O—O—(C=O)—R. The peroxide decomposes to give R., known as a free radical, which reacts with olefin monomer to begin the polymerization cycle. Taking tetrafluoroethylene as an example:

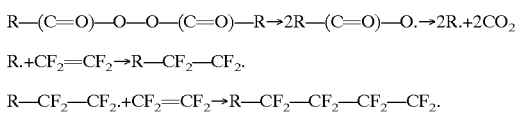

The R group arising from the initiator is called an "endgroup" of the polymer.

The classical synthesis of diacyl peroxides is an aqueous synthesis. An alkaline aqueous solution of hydrogen peroxide is contacted with a water-immiscible solution of acid halide. Examples are found in S. R. Sandler and W. Karo, (1974) *Polymer Synthesis*, Vol. 1, Academic Press, Inc., Orlando Florida, p. 451 and U.S. Pat. No. 5,021,516. This is a reaction of two liquid phases, an aqueous phase and a nonaqueous phase. Equation (1) shows the reaction:

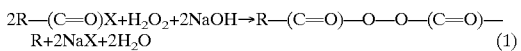
(1)

From the stoichiometry of (1) it is clear that one mole of hydrogen peroxide reacts with two moles of acyl halide to yield one mole of diacyl peroxide. The acyl halide is added in a solvent that has low water solubility. The diacyl peroxide as it forms is taken up in the solvent. By this means, exposure of the acyl halide and the diacyl peroxide to the alkaline aqueous phase is minimized, which is desirable because water hydrolyzes both the organic acyl halide starting material and the diacyl peroxide product. Hydrolysis decreases yield and introduces byproducts such as acids and peracids, which are impurities. At the end of the reaction, the nonaqueous solvent with the diacyl peroxide dissolved in it is separated and dried, and purified as necessary.

Carbon dioxide ($CO_2$) is among the most economical and environmentally benign nonaqueous solvents for polymerization. Polymerization in $CO_2$ is simplified if initiator can be supplied in $CO_2$. The use of diacyl peroxides in liquid or supercritical carbon dioxide is known (J. T. Kadla, et al., *Polymer Preparation*, vol. 39, no. 2, pp. 835–836, 1998). However, the peroxides were prepared using the aqueous alkaline peroxide method and were taken up in $CF_2Cl$—$CFCl_2$ (CFC—113). Only then were they added to carbon dioxide.

A direct synthesis of diacyl peroxides in carbon dioxide is needed.

SUMMARY OF THE INVENTION

One form of this invention relates to a process for the synthesis of diacyl peroxide comprising contacting organic acyl halide with peroxide complex, in liquid or supercritical carbon dioxide.

A second form of this invention relates to a process for the continuous synthesis of diacyl peroxide comprised of continuously contacting a feed stream comprised of organic acyl halide in liquid or supercritical carbon dioxide with a bed comprised of peroxide complex, to form a product stream comprised of diacyl peroxide in liquid or supercritical carbon dioxide.

DETAILED DESCRIPTION OF THE INVENTION

The present invention relates to the synthesis of diacyl peroxide in liquid or supercritical carbon dioxide by contacting organic acyl halide with peroxide complex in a medium of liquid or supercritical carbon dioxide. As stated above, the usual synthesis of diacyl peroxides is by reaction of aqueous alkaline peroxide with acyl halide. Surprisingly, it has been found that carbon dioxide, a Lewis acid, is an effective solvent for the production of diacyl peroxide by the reaction of acyl halide with peroxide complex. In addition, in a preferred form of the invention, liquid or supercritical carbon dioxide containing the resulting diacyl peroxide is collected as a product of the reaction. This mixture can be directly used in other processes, e.g., initiator supply for polymerization in carbon dioxide. This form of the invention provides a route to the direct synthesis in good yield of diacyl peroxides in carbon dioxide, minimizing the presence of water and eliminating any other organic solvent as would be inevitable in synthetic routes that would prepare the diacyl peroxide first in another solvent, and subsequently replacing that solvent, by whatever means, with carbon dioxide.

Organic acyl halides are compounds of the structure R—(C=O)X. X represents halogen: fluorine, chlorine, bromine, or iodine. The most readily available acyl halides are generally acyl chloride or acyl fluoride. R represents any organic group that is compatible with one or more of the peroxide complexes useful for carrying out this invention under the conditions of the synthesis. A compatible R group is one that does not contain atoms or groups of atoms that are susceptible to oxidation by or otherwise react with the other ingredients in the course of the reaction or in the reaction mixture to give undesirable products. R groups acceptable in the present invention include aliphatic and alicyclic groups, these same groups with ether functionality, aryl groups and substituted aryl groups in which the substituents are compatible with one or more of the peroxide complexes of this invention under the conditions of the synthesis. The R group may be partially or completely halogenated. If perhalogenated, the R group may have only one type of halogen, as with perfluorinated groups, or may have several types, as with, for example, chlorofluorinated groups.

The R group may also contain certain functional groups or atoms such as —$COOCH_3$, —$SO_2F$, —CN, I, Br, or H. The R group is incorporated in the polymer at the end of the polymer chain, that is, as an endgroup. It is sometimes useful to be able to further react the polymer through the endgroup with other molecules, for example, other monomers or polymer, or to introduce ionic functionality in the endgroup for interaction with polar surfaces such as metals, metal oxides, pigments, or with polar molecules, such as water or alcohols, to promote dispersion. Some of the functional groups above, for example —$COOCH_3$ and —$SO_2F$ (the fluorosulfonyl group), are susceptible to hydrolysis, especially base-catalyzed hydrolysis, and reaction with nucleophiles. However, because of the absence of an aqueous phase in a preferred form of this invention and of the specificity of the peroxide complexes useful in carrying out this invention, these functional groups are not affected and the diacyl peroxides corresponding to these acyl halides can be made. For example, from $FSO_2CF_2(C=O)F$, $FSO_2CF_2(C=O)$—O—O—$(C=O)CF_2SO_2F$ can be made without hydrolysis of the sulfonyl fluoride functionality to sulfonic acid. It is a further advantage of the process according to this invention that such hydrolysis-sensitive groups can be incorporated in diacyl peroxides and thereby introduced as endgroups in polymers.

In the synthesis of diacyl peroxide in accordance with this invention, no more than one organic acyl halide will normally be used. Although with more than one organic acyl halide the reaction would proceed satisfactorily, more than one diacyl peroxide would be made. For example, if two organic acyl halides are used, A—(C=O)X and B—(C=O)X, three diacyl peroxides would be expected: A—(C=O)—O—O—(C=O)—A, B—(C=O)—O—O—(C=O)—B, and A—(C=O)—O—O—(C=O)—B, a mixed diacyl peroxide. The ratio of the peroxides can be controlled to some extent by the relative concentrations and order of addition of the organic diacyl halides. Such a mixture of peroxides is usually undesirable because the different peroxides will generally have different decomposition rates. However, if a mixed diacyl peroxide is wanted, the process according to this invention may be used, followed if necessary by separation or purification steps to reduce or remove the accompanying unwanted peroxides.

Diacyl peroxides in which the acyl group is a hydrocarbon group can be made according to this invention. These hydrocarbon diacyl peroxides are useful for initiation of olefin polymerization, including fluoroolefin polymerization when the presence of a hydrocarbon endgroup is acceptable or desirable. Isobutyryl peroxide is preferred when a low temperature hydrocarbon initiator is needed. It can be made from isobutyryl halide, preferably isobutyryl chloride.

Synthesis of diacyl peroxides according to this invention is particularly useful for making initiators for the polymerization of fluoroolefins such as tetrafluoroethylene, hexafluoropropylene, perfluoro(alkyl vinyl ethers), chlorotrifluoroethylene, vinylidene fluoride, and vinyl fluoride, either as homopolymers, or as copolymers with each other or with other olefins, such as ethylene and perfluoroalkylethylenes. Fluoroolefin polymerization is susceptible to chain transfer if compounds with labile carbon-hydrogen bonds are present, so it is desirable that initiators be free of such bonds. Furthermore, because of the high temperatures at which fluoropolymers are processed and used, the thermal and hydrolytic stability of the polymer endgroups is important. The R group of the initiator is one source of such endgroups. Therefore, except in cases where specific reactivity of polymer endgroups is wanted, in the interest of minimizing chain transfer activity of the initiator and of providing endgroups with thermal and hydrolytic stability comparable to that of the polymer chain, it is desirable that the R group be free of bonds that are capable of chain transfer or that are less thermally or hydrolytically stable than the polymer itself. In polymerizing fluoromonomers, perhalogenated R groups, and preferably perfluorinated R groups, meet this requirement. Because ether functionality in halogenated and fluorinated organic groups has good thermal and oxidative stability if the oxygen is between carbon atoms that are perhalogenated or perfluorinated, or between carbon atoms that are substituted with perhaloalkyl or perfluoroalkyl groups, such ether functionality is acceptable also.

It is a further advantage of diacyl peroxide synthesis in accordance with this invention that fluoroorganic acyl halides, that is, acyl halides in which the R group is at least partially fluorinated, and particularly perfluoroorganic acyl halides, are readily reacted to form the corresponding diacyl peroxides. An example of a perfluoroorganic acyl halide useful for this invention is perfluoro(2-methyl-3-oxa-hexanoyl fluoride), also known as hexafluoropropylene oxide (HFPO) dimer acid fluoride and as DAF. It has the formula:

$CF_3CF_2CF_2OCF(CF_3)(C=O)F$

Other suitable perfluoroorganic acyl halides include $CF_3CF_2CF_2(C=O)Cl$ (heptafluorobutyryl chloride) and $CF_3CF_2(C=O)F$ (pentafluoropropionyl fluoride).

The peroxide complexes useful for carrying out this invention include a) complexes of hydrogen peroxide with inorganic compounds, referred to here as inorganic complexes, and b) complexes of hydrogen peroxide with organic molecules, referred to here as organic peroxide complexes. These complexes include those substances in which hydrogen peroxide is combined with inorganic or organic compounds by bonds strong enough to permit isolation of the compounds, though the bonds may be weaker or of a different character than those between the constituents of hydrogen peroxide or of the compound with which it is complexed. By this criterion it can be seen that "sodium percarbonate", which is isolable and has the composition $Na_2CO_3.1\frac{1}{2}H_2O_2$, is a complex of hydrogen peroxide, while an aqueous solution of hydrogen peroxide, although it may have degrees of hydration that vary with concentration, is not. Complexes, as the term is used here, also include compounds such as sodium perborate, in which the elements of peroxide are reported to be an integral part of the molecule. The complexes according to this invention do not include persulfates or monopersulfates, such as potassium monopersulfate ($KHSO_5$), which are found to be ineffective. It is believed that the stability oxygen-sulfur bond in the persulfate is so great that persulfates cannot provide the elements of hydrogen peroxide needed for this synthesis. Apart from these stipulations, nothing is implied as to the structure of the complexes. They may be combinations of hydrogen peroxide with the inorganic compound or organic molecule in which the peroxide is associated through weak or strong bonds. Alternatively, they may be reaction products of peroxide with the compound or molecule, in which elements of the peroxide are incorporated in the structure of the compound or molecule, but are available for reaction with acid halides. For some complexes, the structures may be unknown. It is preferable that the complexes be dry. It is more preferable that the complexes be anhydrous. The term "dry" means essentially free of water, though water of crystallization may be present. "Anhydrous" means essentially free of water including water of crystallization. A number of peroxide complexes and their syntheses are described in U.S. Pat. No. 5,820,841.

It is preferred for the peroxide complex to be substantially insoluble in liquid or supercritical carbon dioxide and to be present during the reaction as a solid phase. Such peroxide complexes are easily removed after reaction by filtration or used in the form of a bed through which the acyl halide in liquid or supercritical carbon dioxide is passed. Similarly, it is also preferred that the spent complex after reaction remain insoluble and in the solid phase.

Among the convenient inorganic peroxide complexes for the synthesis of diacyl peroxides according to this invention are percarbonate and perborate salts. These are most readily available as the sodium salts, which are used in the detergent industry. The other alkali metal salts of percarbonate or perborate, as for example, the potassium salts, may also be used in accordance with the processes of this invention. Those skilled in the art will recognize that the alkaline earth percarbonates and perborates, as for example, the calcium salts, though less desirable because less readily available, would be expected to be useful according to the processes of this invention. For the purposes of this invention, although both the alkali metal and alkaline earth percarbonates and perborates have utility in the synthesis of diacyl peroxides, the alkali metal salts are preferable, and the sodium salts are more preferable. For convenience, the percarbonate salts and perborate salts will be referred to herein simply as percarbonate and perborate.

Sodium percarbonate, $Na_2CO_3.1½H_2O_2$, is hydrolyzed by moisture, and for best results in the synthesis of diacyl peroxide according to this invention, the percarbonate should be kept dry. Sodium perborate, though represented as $NaBO_3.H_2O$ and sometimes called sodium perborate monohydrate, is reported to be $Na_2(B_2O_8H_4)$, and is therefore an anhydrous salt. Analogously, the so-called sodium perborate tetrahydrate is reported to be the trihydrate: $Na_2(B_2O_8H_4).3H_2O$. The misnamed sodium perborate monohydrate is the preferred form to be used in the practice of this invention.

The organic peroxide complexes of this invention include those that may have some solubility in carbon dioxide, or at least be volatile enough to make separation from carbon dioxide difficult. The preferred organic complexes are those that are insoluble and whose residues are insoluble in carbon dioxide, and which are present during the synthesis as a solid phase. As such, they are easily separated from the diacyl peroxide solution. It is further desirable that the organic complexes be free of labile atoms or groups, or of bonds that can react with the reactants or products of the processes according to this invention, especially if such reactions degrade the organic molecule and such degradation products get into the reaction mixture.

Urea/hydrogen peroxide adduct (urea.$H_2O_2$) is a more preferred organic peroxide complex. It is commercially available (Aldrich Chemical Co. Milwaukee, Wis., USA). It is a solid and is essentially insoluble in the solvents designated herein and should small amounts be carried through filters or by other means into the diacyl peroxides solution, urea, not being active toward free-radical chain transfer, will have little or no effect on polymerization.

A significant advantage of organic peroxide complexes is that they introduce no metal ions into the reaction mixture and therefore give diacyl peroxide free of metal ions derived from the reactants. In polymerization, such diacyl peroxide made from organic peroxide complexes will introduce no metal ions into the polymer. Polymers, especially fluoropolymers, of low metal content, or free of metal ions, are needed for certain applications where high purity is required, such as the semiconductor industry.

An important characteristic of percarbonate, perborate, and urea/hydrogen peroxide adduct of this invention, and of the carbonate, borate, and urea remaining after the reaction, is their insolubility in carbon dioxide and because they are in the solid phase during the synthesis. Because they are solids, they can be easily separated from reaction mixtures by filtration. For the same reason, percarbonate, perborate, and urea/hydrogen peroxide adduct may be used in fixed beds for continuous synthesis of diacyl peroxides.

The temperature of the reaction is chosen to balance the interest in having a fast reaction with the need to prevent excessive loss of diacyl peroxide through thermal decomposition. Because diacyl peroxides vary in half-life (the time for one-half of the diacyl peroxide to be consumed; half-life is a function of temperature) reaction temperatures will vary, but useful temperatures are in the range of about −40° C. to about 40° C. For peroxides such as HFPO dimer peroxide, heptafluorobutyryl peroxide, isobutyryl peroxide, and bis[perfluoro(fluorosulfonyl)acetyl] peroxide, a temperature range of about −20° C. to about 20° C. is typical, about −10° C. to about 10IC is preferred, and about −5° C. to about 5° C. is more preferred when sodium percarbonate or sodium perborate is used. When urea/hydrogen peroxide adduct is used to make these diacyl peroxides, about −0° C. to about 10° C. is the more preferred temperature. Diacyl peroxide loss to thermal decomposition is best minimized by keeping reaction time a fraction of the diacyl peroxide's half-life at reaction temperature. A reaction time no greater than one-quarter of the diacyl peroxide half-life at the reaction temperature is preferred.

Because residual acyl halide is an impurity in the product diacyl peroxide, and is furthermore a source of acid that can cause corrosion, it is desirable to conduct the synthesis so as to yield as much of the diacyl peroxide as possible. Yield is preferably at least about 25%, more preferably at least about 50%, more preferably still at least about 70%, and most preferably at least about 90%.

The carbon dioxide used as solvent according to this invention will be in the liquid state at the preferred reaction temperatures for the synthesis of preferred diacyl peroxides. However, if it is desired to run the reaction at temperatures above the critical temperature of carbon dioxide, 31° C., that can be done, in which case carbon dioxide in its supercritical state.

When diacyl peroxide is synthesized according to this invention in a batchwise manner, the reactant organic acyl halide is mixed with peroxide complex in a vessel containing a medium comprised of carbon dioxide. Surprisingly, it is found that the yield of diacyl peroxide increases as the mole ratio of peroxide in the peroxide complex to acyl chloride increases. It is preferable that the mole ratio be at least about one to one. It is more preferable that the mole ratio be at least about two to one. It is most preferable that the mole ratio be at least about four to one. Because the peroxide content of the peroxide complex depends upon the nature of the complex, the weight of complex that contains a mole of peroxide or its equivalent will depend upon the composition of the complex under consideration.

To prepare diacyl peroxide in a continuous reaction according to this invention, a feed stream comprised of organic acyl halide in liquid or supercritical carbon dioxide is continuously contacted with a bed comprised of peroxide complex to form a product stream comprising diacyl peroxide in liquid or supercritical carbon dioxide. The bed may be in the form of a column filled with peroxide complex and optionally an inert material. The purpose of the inert material would be to facilitate flow and temperature control. As stated above, the synthesis should be run so as to achieve high yield of the diacyl peroxide. The continuous method is preferred because it allows diacyl peroxide to be made as needed and consumed promptly. If desired, the diacyl peroxide in the liquid or supercritical carbon dioxide can be collected and advantageously used directly in that form. The continuous process ensures that fresh diacyl peroxide is always available and eliminates the need for diacyl peroxide storage, which generally requires low temperatures, and is therefore vulnerable to power outages and equipment failure. Furthermore, as with any oxidizing agent, it is sound practice to minimize the quantities of diacyl peroxide kept on hand. Both batch and continuous methods are demonstrated in the Examples.

Diacyl peroxide made according to this invention may be used in carbon dioxide to initiate polymerization. However, it is one of the advantages of making the initiator in carbon dioxide that the initiator may be conveniently transferred to another solvent by adding the initiator in carbon dioxide to said solvent and letting the carbon dioxide vaporize away. Any traces of carbon dioxide remaining can be removed if necessary by sparging, for example with nitrogen, or under reduced pressure. Using this "solvent transfer method", diacyl peroxide solutions of any desired concentration can be safely and easily made, even in solvents that would not be suitably used in the synthesis of the diacyl peroxide. Thus, the diacyl peroxide synthesis in carbon dioxide according to this invention can be the source of initiator solutions in a wide variety of solvents.

EXAMPLES

Glossary

HFPO=Hexafluoropropylene oxide
HFPO Dimer Peroxide=$CF_3CF_2CF_2OCF(CF_3)(C=O)OO(C=O)(CF_3)CFOCF_2CF_2CF_3$
HFPO Dimer Acid Fluoride=$CF_3CF_2CF_2OCF(CF_3)(C=O)F$
DAF=HFPO Dimer Acid Fluoride
Vertrel® XF=$CF_3CFHCHFCF_2CF_3$ (2,3-dihydroperfluoropentane) available from the DuPont Company, Wilmington, Del., USA

Test Method

Diacyl peroxides formed by this process are analyzed by peroxide titration using the following standard procedure. In a loosely stoppered Erlenmeyer flask, several grams of dry ice are added to 25 ml of glacial acetic acid. This is done to flush oxygen from the system. 5.0 ml of a solution of 30 g of potassium iodide in 70 ml of deoxygenated water is added, and then 5.0 ml of the peroxide solution to be analyzed is added. The mixture is stirred for 30 minutes to allow the peroxide to react with the iodide. 100 ml of deoxygenated water is added and the reaction mixture, having a deep iodine color, is titrated to light yellow with 0.1N sodium thiosulfate. Then 0.5 g of Thyodene® (Fisher Scientific Co.) iodometric indicator is added making the reaction mixture turn blue. Titration is continued with 0.1N sodium thiosulfate to a colorless endpoint. The molar peroxide concentration is 0.01 times the total number of ml of 0.1N sodium thiosulfate solution added to the reaction.

Example 1

HFPO Dimer Peroxide Synthesis in Liquid Carbon Dioxide

A 300 ml stainless steel autoclave, equipped with a paddle stirrer and dip tube, is dried by heating to 100° C. for several hours under a dry nitrogen purge. Dry sodium percarbonate ($Na_2CO_3 \cdot 1\frac{1}{2}H_2O_2$) (2 g (12.7 mmol)) is added and the autoclave is sealed, evacuated, and chilled to about −20° C.

Separately, a 1-liter stainless steel cylinder is charged with 5.2 ml (24.7 mmol) of HFPO dimer acid fluoride (DAF). The cylinder is cooled on dry ice and evacuated, and about 220 g of carbon dioxide is admitted. The cylinder is then connected to the autoclave using ⅛ inch (3.2 mm) diameter stainless steel tubing. The cylinder is inverted to transfer the entire contents of the cylinder to the autoclave. Prior vacuum of the autoclave and prior chilling of the autoclave promotes good transfer. About 199 g of the HFPO dimer acid fluoride/liquid carbon dioxide mix is transferred from the stainless steel cylinder into the autoclave.

The contents of the autoclave are stirred at about 5000 rpm for four hours at 0° C. Temperature fluctuates mildly during this time from −2° C. to 0.5° C. The internal pressure in the autoclave varies from 477 psi (3.29 MPa) at −2° C. to 520 psi (3.59 MPa) at 0.5° C. After about four hours, the autoclave is chilled to −27° C. with the contents still stirring. Chilling to −27° C. reduces the internal pressure of the autoclave to 184 psi (1.27 MPa). A 1-liter pressure-resistant cylinder is evacuated and cooled in a liquid nitrogen bath. The cylinder is then connected to the dip tube outlet on the autoclave using an 18 inch (45 cm) length of ⅛ inch (3.2 mm) diameter stainless steel tubing. The contents of the autoclave are then vented into the stainless steel cylinder through the dip tube. At the end of the transfer, the pressure in the cylinder is 0.2 atm (20 kPa). A valve on the top of the cylinder is removed and 100 ml of Vertrel® XF is added so that the diacyl peroxide in the carbon dioxide can be transferred into the Vertrel® XF to facilitate measurement of reaction yield. The valve is replaced on the cylinder. The cylinder is removed from the liquid nitrogen bath. Contents of the cylinder are allowed to warm until rapid carbon dioxide evolution ceases. Evolution of carbon dioxide is judged by periodically opening and closing the cylinder valve and noting pressure changes.

Once carbon dioxide is no longer being rapidly evolved and frost on the sides of the cylinder shows the first signs of thawing (about 30–45 minutes), the valve is removed from the top of the cylinder. Contents of the cylinder, a hazy gray/blue fluid, are poured into a polyethylene bottle chilled on dry ice.

Opening the 300 ml autoclave at this point reveals residual white solid on the bottom and traces of white film on the walls of the autoclave. On visual inspection, the amount of solids left in the autoclave is observed to be approximately the same volume as the amount of sodium percarbonate added at the start.

The gray/blue fluid recovered from the reactor measures 85 ml in volume. Peroxide titration of 5.0 ml takes 5.95 ml of 0.1 N thiosulfate. This titration corresponds to a 41% yield of HFPO dimer peroxide.

The remaining gray/blue fluid, measuring 80 ml, is warmed from −78° C. to room temperature and washed three times in a separatory funnel with water. This water wash removes any unreacted sodium percarbonate and hydrogen peroxide that would titrate the same as the HFPO dimer peroxide. A 5 ml aliquot of the solution now takes 6.40 ml of 0.1 N thiosulfate in peroxide titration (the increase in peroxide concentration may reflect some evaporation of the Vertrel® XF solvent during the water wash).

Example 2

Continuous Synthesis of HFPO Dimer Peroxide in Liquid Carbon Dioxide

A 150 ml stainless steel cylinder is evacuated and charged with 7.90 g of perfluoro(2-methyl-3-oxa-hexanoyl) fluoride ($CF_3CF_2CF_2OCF(CF_3)COF$) ("DAF") and 50 g carbon dioxide. The cylinder, equipped with a pressure gauge is inverted and placed in a stand fixed to a balance. ¹⁄₁₆ inch (1.6 mm) diameter stainless steel tubing is connected from the cylinder to the top of a stainless steel column about 0.56 cm in diameter and 10 cm in length. The column is packed with 10.0 g of sodium percarbonate. A plug of glass wool at the bottom of the column keeps the sodium percarbonate in the column. The column is immersed in a constant temperature bath at 0° C. A short length of 1/16 inch (1.6 mm) stainless steel tubing runs from a valve at bottom of the column, through a rubber septum, and into a cold trap that is immersed in a dry-ice/acetone slurry and vented to the atmosphere. The trap contains about 50 g Vertrel® XF.

The cylinder valve is opened allowing the liquid DAF/ $CO_2$ mixture to fill the column. The valve between the bottom of the column and the cold trap is then opened slightly to permit a controlled flow of material through the column at a rate of 0.154 g/min. The void volume in the column is 6.0 ml. The void volume divided by the flow rate of material through the column is taken as the contact time. The contact time is 39 minutes. The non-volatile effluent from the column is taken up in the cold trap to form a solution in Vertrel® XF. The low temperature of the trap preserves the diacyl peroxide formed, and the solvent provides a convenient medium for subsequent product analysis. Most of the $CO_2$ is vented spontaneously to the atmosphere from the trap. At the conclusion of the experiment, the cold trap is warmed to 0° C. in ice water and vigorously agitated until the weight of the trap remains constant to remove any remaining $CO_2$. Peroxide titration of aliquots of solution from the cold trap shows that 4.81 g of peroxide is formed. Its identity is confirmed from absorption at 1881 cm$^{-1}$ and 1829 cm$^{-1}$ in its infrared spectrum arising from carbonyl groups in the diacyl peroxide. The amount of DAF remaining in the collected product is 2.19 g as determined from the intensity of the infrared absorption at 1881 cm$^{-1}$ arising from the acid fluoride carbonyl group. From these data a yield of peroxide is calculated to be 68.7%.

Example 3

Continuous Synthesis of HFPO Dimer Peroxide in Liquid Carbon Dioxide

The procedure and equipment are as described in Example 2 except the 4.74 g DAF is charged in the cylinder, the feed rate is 0.129 g/min, and the contact time is 46 minutes. Product collected is 4.02 g, and 0.67 g remains on the column. The product consists of 2.94 g peroxide and 1.41 g of recovered DAF. Yield is 67.6%.

Example 4

Continuous Synthesis of HFPO Dimer Peroxide in Liquid Carbon Dioxide

The procedure and equipment are as described in Example 2. The feed rate is 0.0697 g/min, and the contact time is 86 minutes. Product collected is 7.01 g and 1.53 g remain on the column. The product consists of 6.23 g peroxide and 0.43 g of recovered DAF. Yield is 93.56%.

Example 5

Continuous Synthesis of HFPO Dimer Peroxide in Liquid Carbon Dioxide

The procedure and equipment are as described in Example 2 except the temperature of the bath around the column is maintained at 10° C., the feed rate is 0.165 g/min, and the contact time is 32 minutes. Product collected is 5.87 g, and 1.89 g remains on the column. The product consists of 5.36 g peroxide and 0.43 g of recovered DAF. Yield is 91.3%.

Example 6

Continuous Synthesis of HFPO Dimer Peroxide in Liquid Carbon Dioxide

The procedure and equipment are as described in Example 2 except the temperature of the bath around the column is maintained at 15° C., the feed rate is 0.242 g/min, and the contact time is 20 minutes. Product collected is 5.92 g, and 1.69 g remains on the column. The product consists of 5.13 g peroxide and 1.02 g of recovered DAF. Yield is 83.4%.

Summary of Examples 2 to 6

Table 1 summarizes the results of the examples of the continuous synthesis of diacyl peroxide. Yields are increased with longer contact time or with higher reaction temperature.

TABLE 1

| Example | Contact Time (min) | Temperature (° C.) | Yield (%) |
|---|---|---|---|
| 2 | 39 | 0 | 68.7 |
| 3 | 46 | 0 | 67.6 |
| 4 | 86 | 0 | 93.6 |
| 5 | 32 | 10 | 91.3 |
| 6 | 20 | 15 | 83.4 |

Example 7

HFPO Dimer Peroxide Synthesis in Carbon Dioxide Using Urea Hydrogen Peroxide Adduct A jacketed autoclave of 125 ml volume is heated to 60° C. and purged with nitrogen for several hours. The autoclave is then cooled to room temperature and 3.0 g (30.9 mmoles $H_2O_2$ equivalent) urea/hydrogen peroxide adduct (Aldrich Chemical Co.), containing 35.0% $H_2O_2$ by peroxide titration, is added under a stream of nitrogen. The autoclave is closed, evacuated, and cooled to −20° C. A cylinder, into which 16.0 g of HFPO dimer acid fluoride (48.2 mmoles) and 60 g of carbon dioxide had been charged, is connected to the autoclave and the contents of the cylinder are transferred into the autoclave. The temperature of the autoclave is then raised to 0° C. while its contents are agitated for 6 hrs. The bottom port of the autoclave is fitted with a sintered metal filter containing 15 micrometer pores to retain urea and unused urea/hydrogen peroxide adduct. The contents of the autoclave are vented into an accurately weighed nitrogen flushed cold trap immersed in a dry ice/acetone bath. The trap contained about 50 g of Vertrel® XF. The solvent is used to absorb the reaction mixture as most of the carbon dioxide is vented to the atmosphere. This also provided a convenient medium for infrared analysis of the reaction mixture at room temperature and atmospheric pressure.

The cold trap and its contents are warmed to 0° C. in an ice bath with shaking to expel remaining carbon dioxide from the Vertrel® XF solution. The trap is dried and weighed and used to determine the weight of the product solution obtained. A portion of the solution is then placed in a liquid infrared cell and its spectrum measured. A reference spectrum of Vertrel® XF previously obtained in the same liquid cell is subtracted from that of the product mixture and intensities of bands occurring at 1858 cm$^{-1}$ and 1829 cm$^{-1}$ for the HFPO dimer peroxide, 1880 cm$^{-1}$ for the HFPO dimer acid fluoride and 1774 cm$^{-1}$ for the HFPO dimer acid are determined. Calibration curves determined from solutions of known concentration are used to calculate the amounts of each compound from the intensity of the appropriate infrared band in the spectrum of the product mixture. We found 60.6% HFPO dimer peroxide, 36.5% HFPO dimer acid fluoride and 3.0% HFPO dimer acid in the product mixture weighing 13.35 g.

Example 8

HFPO Dimer Peroxide Synthesis in Carbon Dioxide Using Urea Hydrogen Peroxide Adduct The procedure given in Example 7 is used except the temperature of the autoclave is raised to 5° C. We found 83.0% HFPO dimer peroxide, 12.5% HFPO dimer acid fluoride and 4.5% HFPO dimer acid in the product mixture weighing 15.32 g.

Example 9

HFPO Dimer Peroxide Synthesis in Carbon Dioxide Using Urea Hydrogen Peroxide Adduct The procedure given in Example 7 is used except the temperature of the autoclave is raised to 10° C. and agitation is continued for 3 hrs. We found 76.1% HFPO dimer peroxide, 15.5% HFPO dimer acid fluoride and 8.4% HFPO dimer acid in the product mixture weighing 12.36 g.

Example 10

HFPO Dimer Peroxide Synthesis in Carbon Dioxide Using Urea Hydrogen Peroxide Adduct The procedure given in Example 7 is used except 2.9 g of urea is added to the autoclave along with urea/hydrogen peroxide adduct to serve as a mild base to absorb HF generated during the reaction. The temperature of the autoclave is also raised to 5° C. We found 81.4% HFPO dimer peroxide, 15.4% HFPO dimer acid fluoride and 3.2% HFPO dimer acid in the product mixture weighing 7.11 g.

Example 11

HFPO Dimer Peroxide Synthesis in Carbon Dioxide Using Urea Hydrogen Peroxide Adduct The procedure given in Example 7 is used except the amount of urea/hydrogen peroxide adduct charged to the autoclave is 5.0 g (51.5 mmoles $H_2O_2$ equivalent) and the temperature of the autoclave is raised to 5° C. We found 87.8% HFPO dimer peroxide, 6.4% HFPO dimer acid fluoride and 5.8% HFPO dimer acid in the product mixture weighing 16.39 g.

Summary of Examples 7 to 11

Table 2 summarizes the results of the examples of the synthesis of diacyl peroxide using urea/hydrogen peroxide adduct. Yields are increased with longer contact time or with higher reaction temperature. Increasing the ratio of urea/hydrogen peroxide adduct to acyl fluoride (DAF) increases yield. Added urea has little or no effect.

TABLE 2

| Example | Contact Time (hour) | Temperature (° C.) | DAF:$H_2O_2$ (mmoles) | Yield (%) |
|---|---|---|---|---|
| 7 | 6 | 0 | 48.2:30.9 | 47.2 |
| 8 | 6 | 5 | 48.2:30.9 | 83.0 |
| 9 | 3 | 10 | 48.2:30.9 | 76.1 |
| 10* | 6 | 5 | 48.2:30.9 | 81.4 |
| 11 | 6 | 5 | 48.2:51.5 | 87.8 |

*Urea added as mild base.

What is claimed is:

1. A process for the synthesis of diacyl peroxide comprising contacting organic acyl halide with peroxide complex, in liquid or supercritical carbon dioxide.

2. The process of claim 1 further comprising collecting liquid or supercritical carbon dioxide containing diacyl peroxide.

3. The process of claim 1 wherein the peroxide complex is selected from the group consisting of inorganic peroxide complexes and organic peroxide complexes and mixtures thereof.

4. The process of claim 1 wherein the peroxide complex is substantially insoluble in liquid or supercritical carbon dioxide and is present during the reaction as a solid phase.

5. The process of claim 1 wherein the peroxide complex is selected from the group consisting of sodium percarbonate, sodium perborate, urea/hydrogen peroxide adduct, and mixtures thereof.

6. The process of claim 1 wherein the mole ratio of hydrogen peroxide in the peroxide complex to organic acyl halide is at least about one-to-one.

7. The process of claim 1 wherein the process is carried out at a reaction temperature between about −40° C. and about 40° C.

8. The process of claim 1 wherein the process is carried out at a reaction temperature between about −20° C. and about 20° C.

9. The process of claim 1 wherein the process is carried out at a reaction temperature between about −10° C. and about 10° C.

10. The process of claim 1 wherein the process is carried out at a reaction temperature selected so that the reaction time is no greater than one-quarter of the diacyl peroxide half-life at the reaction temperature.

11. The process of claim 1 wherein the organic acyl halide selected from the group consisting of fluoroorganic acyl halides.

12. The process of claim 1 wherein the organic acyl halide is selected from the group consisting of perfluoroorganic acyl halides.

13. The process of claim 1 wherein the organic acyl halide is isobutyryl halide.

14. A process for the continuous synthesis of diacyl peroxides comprised of continuously contacting a feed stream comprised of organic acyl halide in liquid or supercritical carbon dioxide with a bed comprised of peroxide complex, to form a product stream comprising diacyl peroxide in liquid or supercritical carbon dioxide.

15. The process of claim 14 in which the peroxide complex is selected from the group consisting of perborate, percarbonate, urea/hydrogen peroxide adduct, and mixtures thereof.

16. The process of claim 14 further comprising collecting said product stream.

* * * * *